United States Patent
Kim et al.

(10) Patent No.: US 9,826,901 B2
(45) Date of Patent: Nov. 28, 2017

(54) ADAPTOR FOR SLIT LAMP MICROSCOPE

(71) Applicants: Dong Kwan Kim, Namyangju-si (KR); Dong Sik Kim, Seoul (KR)

(72) Inventors: Dong Kwan Kim, Namyangju-si (KR); Dong Sik Kim, Seoul (KR)

( * ) Notice: Subject to any disclaimer, the term of this patent is extended or adjusted under 35 U.S.C. 154(b) by 0 days.

(21) Appl. No.: 15/116,492

(22) PCT Filed: Feb. 3, 2015

(86) PCT No.: PCT/KR2015/001105
§ 371 (c)(1),
(2) Date: Aug. 3, 2016

(87) PCT Pub. No.: WO2015/115877
PCT Pub. Date: Aug. 6, 2015

(65) Prior Publication Data
US 2017/0007124 A1    Jan. 12, 2017

(30) Foreign Application Priority Data
Feb. 3, 2014   (KR) .................. 20-2014-0000737 U

(51) Int. Cl.
*A61B 3/14*   (2006.01)
*A61B 3/135*  (2006.01)
*G02B 21/36*  (2006.01)

(52) U.S. Cl.
CPC ................ *A61B 3/135* (2013.01); *A61B 3/14* (2013.01); *G02B 21/362* (2013.01)

(58) Field of Classification Search
CPC .................................. A61B 3/135; A61B 3/14
USPC ......................................................... 351/206
See application file for complete search history.

(56) References Cited

U.S. PATENT DOCUMENTS

2011/0202017 A1    8/2011   Reimer

FOREIGN PATENT DOCUMENTS

| JP | 08-136817 A | 5/1996 |
| JP | 2011-177501 A | 9/2011 |
| KR | 10-2007-0113539 A | 11/2007 |
| KR | 10-2012-0094232 A | 8/2012 |

*Primary Examiner* — Jack Dinh
(74) *Attorney, Agent, or Firm* — Maschoff Brennan

(57) ABSTRACT

The present invention relates to an adaptor for a slit lamp microscope. According to one embodiment of the present invention, the invention provides the advantages of: facilitating the maintenance/repair of a slit lamp microscope since a camera member used for the slit lamp microscope is simply attached or detached; simply and easily inspecting and photographing a subject's eye; and obtaining a high-resolution video or image for the subject's eye at low costs.

8 Claims, 8 Drawing Sheets

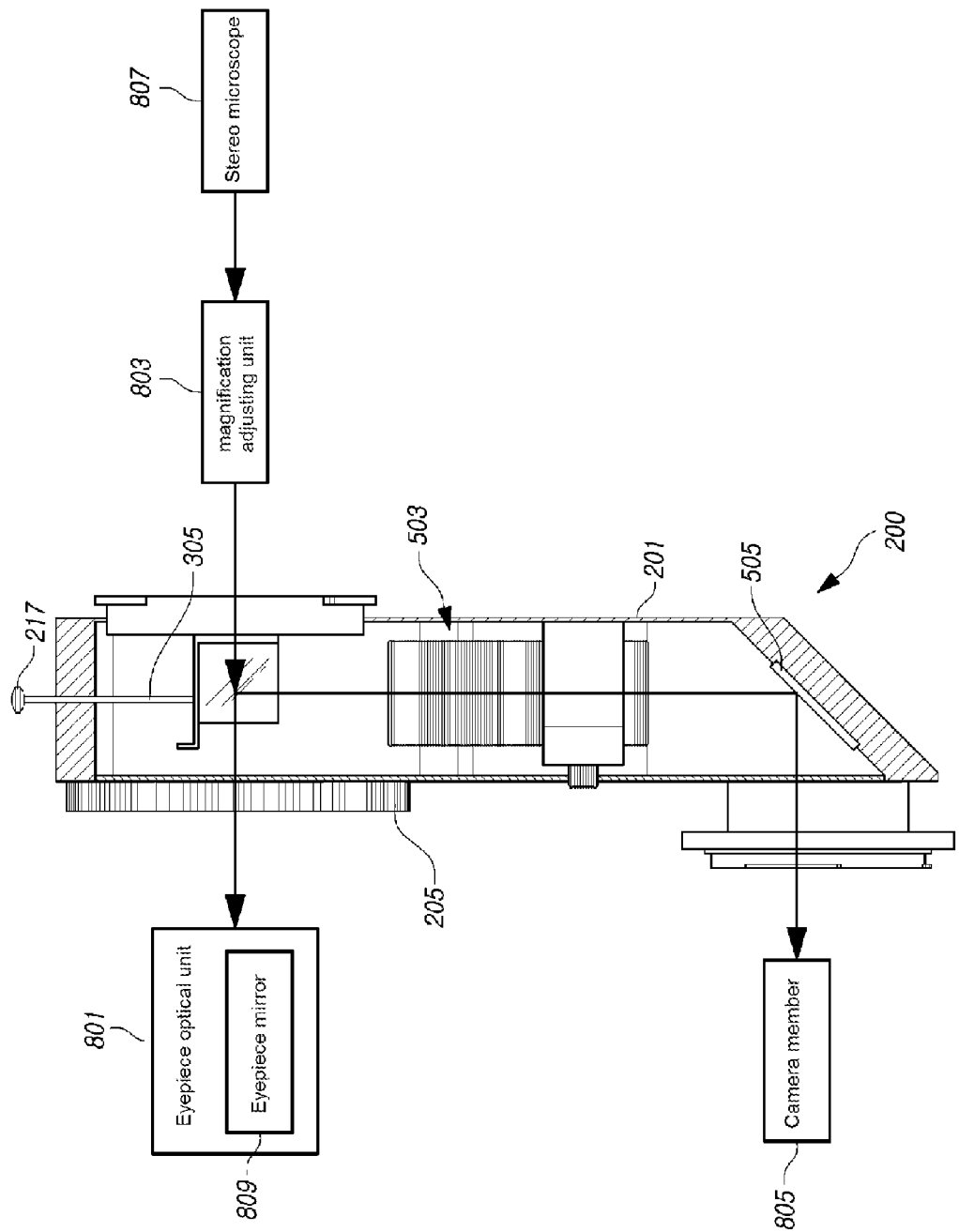

ADAPTOR FOR SLIT LAMP MICROSCOPE

TECHNICAL FIELD

The present invention relates to an adaptor coupled to a slit lamp microscope.

BACKGROUND ART

A slit lamp microscope is a device which is able to examine the states of eyes in such a way to examine an optical cut surface of eyes by radiating a vertically long and thin light (a measuring light) with respect to almost transparent eye tissues.

The aforementioned slit lamp microscope is able to examine an eyelid, a conjunctive, a cornea, an anterior chamber, a lens, a vitreous body (a hyaline body), etc. in such a way to adjust the width, length and angle of a radiated light, and it is possible to even examine a fundus using a predetermined auxiliary equipment.

Moreover, the slit lamp microscope may be used when it needs to take a picture of an anterior segment and measure an anterior chamber depth and the thickness of a cornea and a lens. Since a tonometer can be attached thereto, it is being widely used at an ophthalmology hospital.

FIG. 1 is a view illustrating the whole exterior configuration of a conventional slit lamp microscope. Referring to FIG. 1, the conventional slit lamp microscope is formed of a lighting optical unit 110 configured to radiate a measuring light to a subject's eye 114, and an observation optical unit 120 configured to observe an optical cut surface formed at the subject's eye 114.

The lighting optical unit 110 is formed of a source light 112 which radiates a slit-shaped measuring light, and a reflection mirror 118 which is able to reflect the measuring light and guide to the subject's eye 114. The observation optical unit 120 is formed of an optical distribution unit 122 which is able to split a signal light reflected off the subject's eye 114, a camera 124 employed to record in the form of an image the signal light split by the optical distribution unit 122, and an eyepiece optical system 126 employed to observe with eyes the signal light split by the optical distribution unit 122.

In case of the aforementioned conventional slit lamp microscope, a maintenance and repair work of such a slit lamp microscope is hard since it is not easy to attach and detach a camera to/from the optical distribution unit.

Moreover, in case of a camera which is used for a conventional slit lamp microscope, a SD camera is employed, for which a resolution is low, and it is hard to recognize an image or a video taken from a subject's eye. In addition, in case where a high resolution camera, for example, a HD camera, is employed, a cost may rise. In order to take a video or an image of a subject's eye, various equipment, for example, a beam splitter, a mount and a camera, a video or image capturing device, a computer, a printer, etc. are inevitably necessary. The procedure for obtaining a video or an image in a physical/software way is complicated.

Disclosure of Invention

Accordingly, the present invention is made in an effort to solve the aforementioned problems. It is an object of the present invention to provide an adaptor for a slit lamp microscope wherein a camera member used at a slit lamp microscope can be easily attached and detached, which makes it easier to do a maintenance and repair of the slit lamp microscope, and an examination of a subject's eye can be easily carried out, and it is easy to take a picture of the subject's eye, and a high resolution video or image with respect to the subject's eye can be obtained at low costs.

The aforementioned objects of the present invention are not limited thereto. It is obvious that other objects not mentioned above may be easily understood from the following descriptions by a person having ordinary skill in the art.

To achieve the above object, according to a preferred embodiment of the present invention, there is provided an adaptor for a slit lamp microscope, which may include, but is not limited to, a housing unit wherein an eyepiece optical unit is coupled to one side of the top thereof, and a magnification adjusting unit is coupled to the other side of the top thereof, and a camera member is coupled to one side of a lower portion thereof; a prism unit which is disposed at an inner, upper portion of the housing unit and is configured to open or block a reflection light transmission route of a subject's eye in order for a reflection light of the subject's eye coming in via the magnification adjusting unit to be transmitted or refracted; a focusing lens unit which is provided at an inner, intermediate portion of the housing unit and is able to adjust the visibility of a reflection light of the subject's eye which has been refracted via the prism unit; and a reflection member which is provided at an inner, lower portion of the housing unit and is configured to transmit the reflection light of the subject's eye to the camera member in such a way to change a transmission route of the reflection light of the subject's eye which has passed through the focusing lens unit.

Moreover, the prism unit may include a prism lens unit; a bracket unit to which the prism lens unit is coupled and fixed; and an adjusting lever one end of which is coupled to the bracket unit, and the other end of which extends outward via the housing unit.

In addition, a stopper unit which is formed protruding in a right angle direction, is disposed at the other end of the adjusting lever.

Furthermore, the focusing lens unit may include a body tube unit which is formed in a hollow shape and includes a lens at an inner side thereof; a support bracket unit wherein the body tube unit passes through and is coupled supported movable in an axial direction, wherein the support bracket unit is coupled to an inner, intermediate portion of the housing unit; and an adjusting roller unit which is disposed at the support bracket unit and is able to move the body tube unit in an axial direction.

Moreover, a first thread part is formed at an outer circumferential surface of the body tube unit, and a second thread part to be thread-engaged with the first thread part is formed at an outer circumferential surface of the adjusting roller unit.

In addition, the adjusting roller unit is coupled rotatable to a rotary shaft which is provided at the support bracket unit.

Furthermore, a through hole is formed at a portion corresponding to the adjusting roller unit of the housing unit.

Moreover, the reflection member is formed of a mirror.

Advantageous Effects of the Invention

According to the present invention, a camera member used at a slit lamp microscope can be easily attached and detached, which makes it easier to do a maintenance and repair of the slit lamp microscope, and an examination of a subject's eye can be easily carried out, and it is easy to take

BRIEF DESCRIPTION OF DRAWINGS

FIG. 8 is a view for describing a use example of an adaptor for a slit lamp microscope according to an embodiment of the present invention.

Best Modes for Carrying out the Invention

Figure 1:
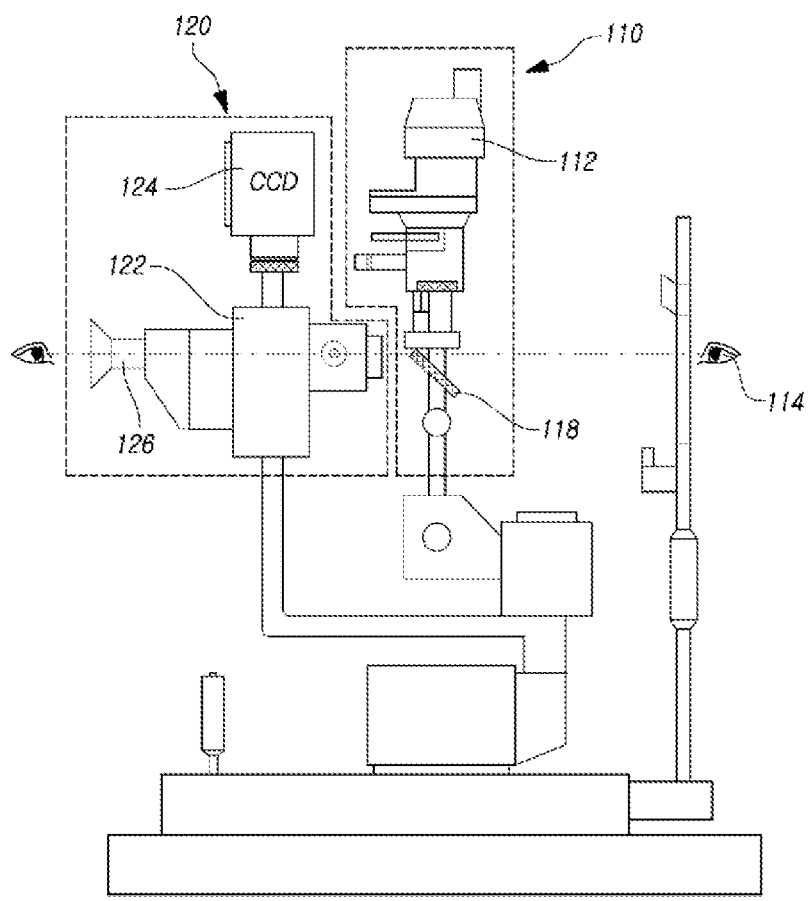
FIG. 1 is a view illustrating the whole exterior configuration of a conventional slit lamp microscope.
Figure 2:
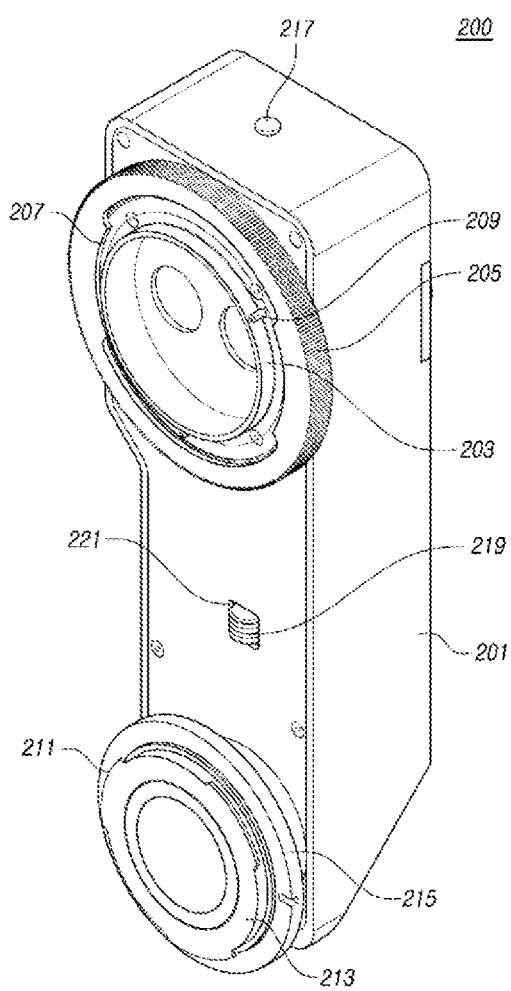
FIG. 2 is a perspective view illustrating an adaptor for a slit lamp microscope according to an embodiment of the present invention.
Figure 3:
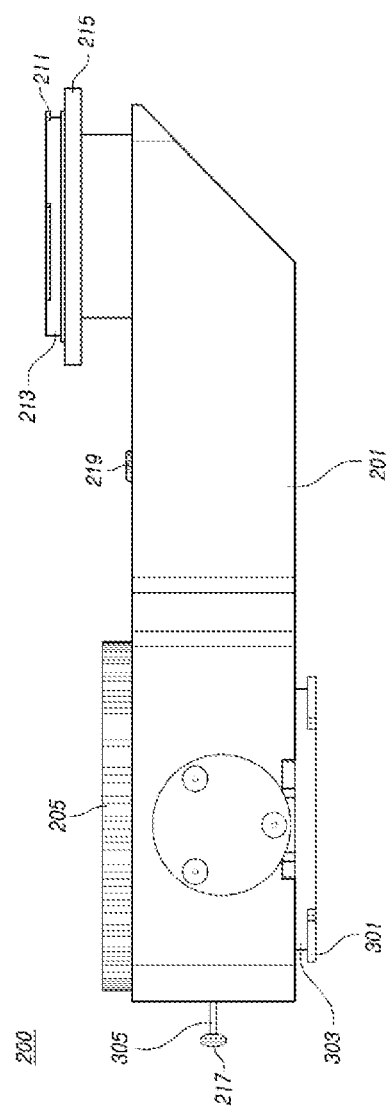
FIG. 3 is a side view illustrating an adaptor for a slit lamp microscope according to an embodiment of the present invention.
Figure 4:
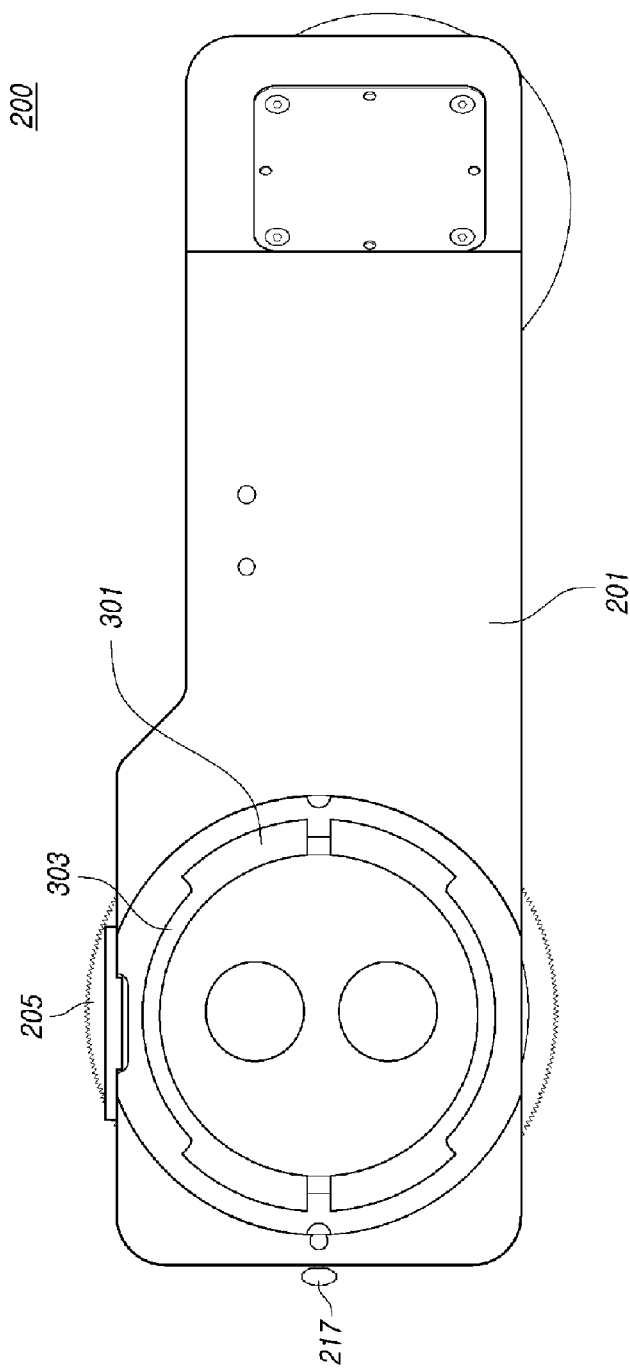
FIG. 4 is a bottom view illustrating an adaptor for a slit lamp microscope according to an embodiment of the present invention.
Figure 5:
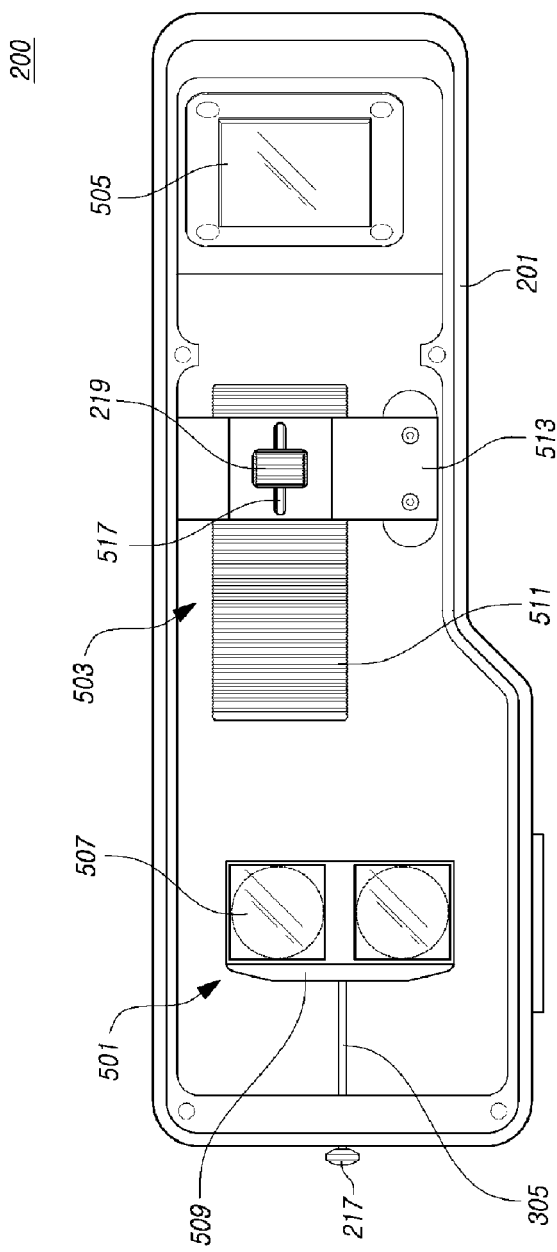
FIGS. 5 and 6 are views illustrating an interior configuration of a slit lamp microscope according to an embodiment of the present invention.
Figure 6:
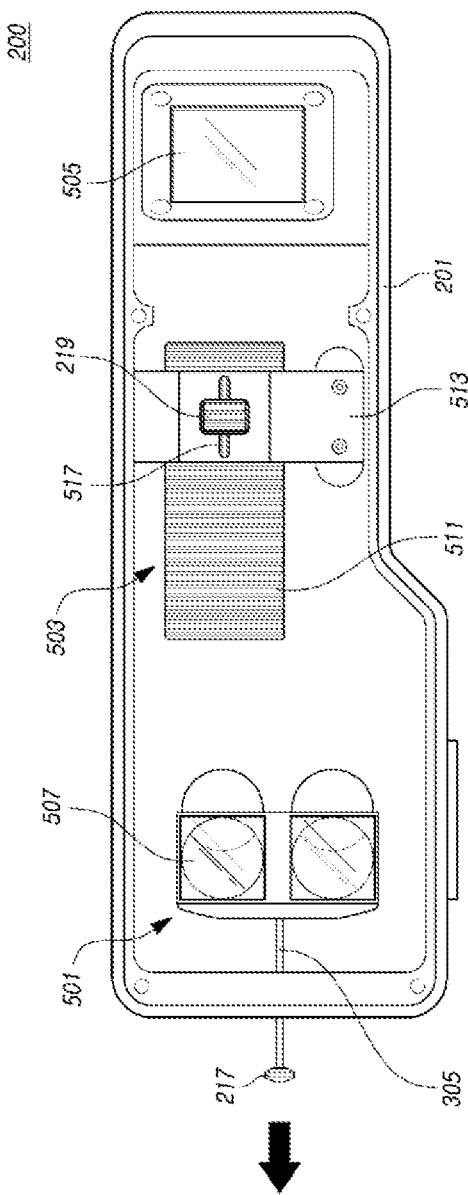
Figure 7:
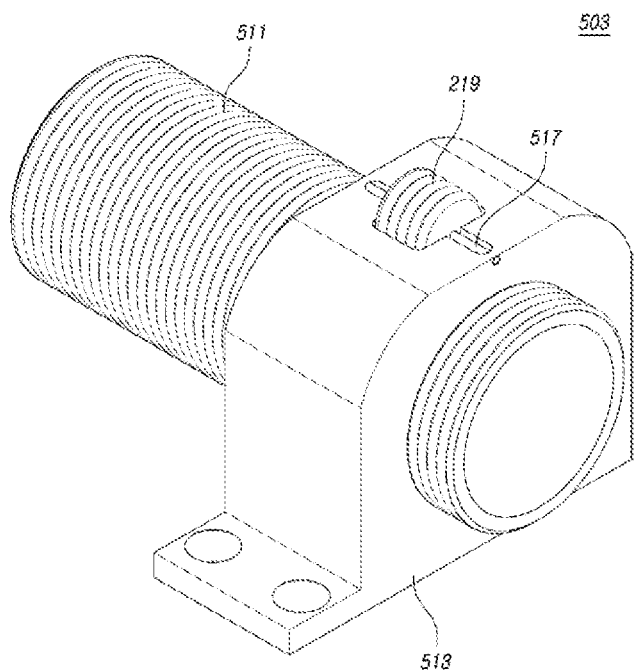
FIG. 7 is a perspective view illustrating a focusing lens unit in FIG. 5.

FIG. 2 is a perspective view illustrating an adaptor for a slit lamp microscope according to an embodiment of the present invention. FIG. 3 is a side view illustrating an adaptor for a slit lamp microscope according to an embodiment of the present invention. FIG. 4 is a bottom view illustrating an adaptor for a slit lamp microscope according to an embodiment of the present invention. FIGS. 5 and 6 are views illustrating an interior configuration of a slit lamp microscope according to an embodiment of the present invention. FIG. 7 is a perspective view illustrating a focusing lens unit in FIG. 5. FIG. 8 is a view for describing a use example of an adaptor for a slit lamp microscope according to an embodiment of the present invention.

As illustrated in the drawings, the adaptor 200 for a slit lamp microscope may include, but is not limited to, a housing unit 201 wherein an eyepiece optical unit 801 is coupled to one side of the top thereof, and a magnification adjusting unit 803 is coupled to the other side of the top thereof, and a camera member 805 is coupled to one side of a lower portion thereof; a prism unit 501 which is disposed at an inner, upper portion of the housing unit 201 and is configured to open or block a reflection light transmission route of a subject's eye in order for a reflection light of the subject's eye coming in via the magnification adjusting unit 803 to be transmitted or refracted; a focusing lens unit 503 which is provided at an inner, intermediate portion of the housing unit 201 and is able to adjust the visibility of a reflection light of the subject's eye which has been refracted via the prism unit 501; and a reflection member 505 which is provided at an inner, lower portion of the housing unit 201 and is configured to transmit the reflection light of the subject's eye to the camera member 805 in such a way to change a transmission route of the reflection light of the subject's eye which has passed through the focusing lens unit 503.

The housing unit 201 is provided, for example, in the form of a box shape. The eyepiece optical unit 801 is coupled to one side of the top of the housing unit 201. A magnification adjusting unit 803 is coupled to the other side of the top thereof, and the camera member 805 is coupled to a lower side thereof.

The eyepiece optical unit 801 is employed for an examiner to examine the states of a subject's eye in such a way to observe the reflection light from the subject's eye. The eyepiece optical unit 801 may include an eyepiece mirror 809 which is detachably coupled to one side of the top of the housing unit 201.

Meanwhile, a guide coupling unit 203 is formed protruding from one side of the top of the housing unit 201. A fixing member 205 is coupled rotatable at the housing unit 201 at an outer side of the guide coupling unit 203.

The fixing member 205 is equipped with a coupling protrusion unit 207 which is more protruding inwardly from the front side, by which the rear side (more specifically, the rear side of the eyepiece lens 809) of the eyepiece optical unit 801 can be engaged with the coupling protrusion part 207.

Moreover, a stopper protrusion 209 is provided at one side of the top of the housing unit 201 so as to limit the rotations of the fixing member 205.

The magnification adjusting unit 801 is equipped with an adjusting handle (not illustrated) to adjust step by step the magnification from a lower magnification to a higher magnification. A magnification adjusting unit coupling unit 303 having a coupling protrusion unit 301 is provided at the other side of the top of the housing unit 201 in order for the magnification adjusting unit 801 to be detachably coupled.

A stereo microscope 807 is coupled to the rear side of the magnification adjusting unit 801.

Moreover, the camera member 805 may be formed of, for example, a digital camera, thus taking a picture of the subject's eye. A camera member coupling unit 213 having a coupling protrusion unit 211 is provided at a lower side of the housing unit 201 in order for the camera member 805 to be detachably coupled. The camera member coupling unit 213 is equipped with a support plate 215 which extends outward in a right angle direction, by which the camera member 805 coupled to the camera member coupling unit 213 can be supported stable.

Since the camera member 805 is coupled detachable to the housing unit 201, the examiner is able to obtain a high resolution image or video with respect to the subject's eye in such a way to use a typical camera that the examiner has, without purchasing a camera.

A prism unit 501 may be provided at an inner, upper portion of the housing unit 201. The prism unit 501 is able to open or block a reflection light transmission route of the subject's eye in order for a reflection light of the subject's eye coming in via the stereo microscope 807 and the magnification adjusting unit 803 to be transmitted or refracted.

An example of the configuration of the prism unit 501 will be more specifically described. The prism unit 501 may include a prism lens unit 507; a bracket unit 509 to which the prism lens unit 507 is coupled and fixed; and an adjusting lever 305 one end of which is coupled to the bracket unit 509, and the other end of which extends outward via the housing unit 201.

The prism lens unit 507 is able to transmit or refract the reflection light of the subject's eye coming in via the magnification adjusting unit 803. The prism lens unit 507 may be configured, for example, to transmit 50% of the reflection light and to refract the remaining 50% of the reflection light.

A bracket unit 509 is employed to fix the prism lens unit 507.

An adjusting lever 305 is configured in such a way that one end thereof is coupled to the bracket unit 509, and the other end thereof extends outward via the housing unit 201. More specifically, the prism lens unit 507 coupled to the bracket unit 509 may open or block the reflection light transmission route of the subject's eye in such a way that the examiner pulls or pushes the adjusting lever 305.

If the prism lens unit 507 opens the reflection light transmission route of the subject's eye as the examiner operates the adjusting lever 305, all the reflection light of the subject's eye will be transmitted to the eyepiece optical unit 801, and if the prism lens unit 507 blocks the reflection light transmission route of the subject's eye, as illustrated in FIG. 8, a part (50%) of the reflection light of the subject's eye is refracted and transmitted to the camera member 805 via a focusing lens unit 503 and a reflection member 505, which will be described later, so the image or video of the subject's eye can be taken using the camera member 805.

Meanwhile, the aforementioned adjusting lever 305 may be formed of a circular pillar-shaped bar. A stopper unit 217 which extends protruding in a right angle direction, may be formed at the other end of the adjusting lever 305 (more specifically, an end portion which extends to the outside of the housing unit 201)), thus allowing the adjusting lever 305 not to insert to the maximum into the inside of the housing unit 201.

The focusing lens unit 503 may be provided at an intermediate portion of the inside of the housing unit 101, and the focusing lens unit 503 is employed to adjust the visibility (a focus) of the reflection light of the subject's eye which has been refracted via the prism unit 501.

An example of the configuration of the focusing lens unit 503 will be described in more details. The focusing lens unit 503 may include a body tube unit 511 which is formed in a hollow shape and includes a lens at an inner side thereof; a support bracket unit 513 wherein the body tube unit 511 passes through and is coupled supported movable in an axial direction, wherein the support bracket unit 513 is coupled to an inner, intermediate portion of the housing unit 101; and an adjusting roller unit 219 which is disposed at the support bracket unit 513 and is able to move the body tube unit 511 in an axial direction.

The body tube unit 511 is formed in a hollow tube shape. A lens (not illustrated) is disposed inside of the body tube unit 511. The lens disposed inside of the body tube unit 511 may be formed, for example, of a convex lens. A first thread part may be provided at an outer circumferential surface of the body tube unit 511.

The support bracket unit 513 may be coupled to an intermediate portion of the inside of the housing unit 101. The body tube unit 511 is supported and engaged to the support bracket unit 513 in such a way that it can be movable in an axial direction via the support bracket unit 513.

An adjusting roller unit 219 is able to move in an axial direction the body tube unit 511. The adjusting roller unit 219 is disposed at the support bracket unit 513.

The aforementioned adjusting roller unit 219 is formed, for example, in a cylindrical shape. A second thread part is formed at an outer circumferential surface thereof so as to thread-engage to the first thread part formed at an outer circumferential surface of the body tube unit 511.

Moreover, the adjusting roller unit 219 is coupled rotatable to a rotary shaft 517 which is provided at the support bracket unit 513. If the examiner rotates the adjusting roller unit 219, the body tube unit 511 will move in an axial direction.

Meanwhile, a through hole 221 may be formed at a portion corresponding to the adjusting roller unit 219 of the housing unit 201. Since the through hole 221 through which the adjusting roller unit 219 is exposed, is formed at the housing unit 201, the examiner can more easily operate the adjusting roller unit 219 when it needs to adjust the position of the body tube unit 511.

Since the examiner adjusts the position of the axial direction of the body tube unit 511 via the operation of the adjusting roller unit 219, a clear image or video of the subject's eye can be taken by the camera member 805 by adjusting the visibility (a focus) of the reflection light of the subject's eye coming in via the prism lens unit 507 after it has been refracted.

The reflection member 505 is provided at an inner, lower end portion of the housing unit 101 and is able to allow the reflection light of the subject's eye to be transmitted to the camera member 805 in such a way to change the transmission route of the reflection light of the subject's eye which has passed through the focusing lens unit 503. The reflection member 505 may be formed of, example, a mirror.

The reflection member 505 is coupled to an inner, lower portion of the housing unit 101 in a state where it is inclined at a predetermined angle in order for the reflection light of the subject's eye to be accurately transmitted to the camera member 805.

As described above, according to an embodiment of the present invention, the camera member used at the slit lamp microscope can be easily attached or detached, so the maintenance and repair of the slit lamp microscope can be easier. The examination of the subject's eye and the photographing of the subject's eye can be easily carried out. A high resolution video or image with respect to the subject's eye can be obtained at lower costs. Meanwhile, if the guide coupling unit and the camera member coupling unit are detachable from the housing unit, the use of the housing unit can be shared when designing the adaptor for various types of slit lamp microscopes, for which the time and cost for the designing can be saved.

Even though all the components belonging to the embodiment of the present invention have been described as being coupled into one form or operating in one form, the present invention is not limited to such embodiment. More specifically, at least one component can be selected from all the components and can be combined and operated within the scope of the present invention.

Unless otherwise stated in the specification, throughout the specification, the term "comprise", "is formed of" or "have" means including a corresponding configuration component, so it should be interpreted as including another configuration component, not excluding such a component. All the terms including a technical or science term, unless otherwise defined, should be interpreted as having the same meaning as the meaning that a person having ordinary skill is able to understand. The terms which are usually used like the terms defined in the dictionary should be interpreted as matching with the meaning according to the given context of the related technology, and unless otherwise defined in the present invention, it should not be interpreted too ideally or excessively.

The above descriptions are provided for the illustrative purposes of the present invention, and it is obvious that a person having ordinary skill in the art is able to variously correct or modify within a scope where the basic features of the present invention are not changed. The embodiments disclosed in the present invention are provided for the sake of detailed descriptions, not intended to limiting the technical concept of the present invention, and the scope of the technical concept of the present invention should not be limited such embodiments. The protection scope of the present invention should be interpreted by the following claims, and all the technical concepts within the equivalent scope should be interpreted as being within the right scope of the present invention.

INDUSTRIAL APPLICABILITY

The present invention can be applied to the adaptor for a slit lamp microscope.

The invention claimed is:

1. A adaptor for a slit lamp microscope, comprising:
    a housing unit wherein an eyepiece optical unit is coupled to one side of the top thereof, and a magnification adjusting unit is coupled to the other side of the top thereof, and a camera member is coupled to one side of a lower portion thereof;
    a prism unit which is disposed at an inner, upper portion of the housing unit and is configured to open or block a reflection light transmission route of a subject's eye in order for a reflection light of the subject's eye coming in via the magnification adjusting unit to be transmitted or refracted;
    a focusing lens unit which is provided at an inner, intermediate portion of the housing unit and is able to adjust the visibility of a reflection light of the subject's eye which has been refracted via the prism unit; and
    a reflection member which is provided at an inner, lower portion of the housing unit and is configured to transmit the reflection light of the subject's eye to the camera member in such a way to change a transmission route of the reflection light of the subject's eye which has passed through the focusing lens unit.

2. The adaptor of claim 1, wherein the prism unit comprises:
    a prism lens unit;
    a bracket unit to which the prism lens unit is coupled and fixed; and
    an adjusting lever one end of which is coupled to the bracket unit, and the other end of which extends outward via the housing unit.

3. The adaptor of claim 2, wherein a stopper unit which is formed protruding in a right angle direction, is disposed at the other end of the adjusting lever.

4. The adaptor of claim 1, wherein the focusing lens unit comprises:
    a body tube unit which is formed in a hollow shape and includes a lens at an inner side thereof;
    a support bracket unit wherein the body tube unit passes through and is coupled supported movable in an axial direction, wherein the support bracket unit is coupled to an inner, intermediate portion of the housing unit; and
    an adjusting roller unit which is disposed at the support bracket unit and is able to move the body tube unit in an axial direction.

5. The adaptor of claim 4, wherein a first thread part is formed at an outer circumferential surface of the body tube unit, and a second thread part to be thread-engaged with the first thread part is formed at an outer circumferential surface of the adjusting roller unit.

6. The adaptor of claim 5, wherein the adjusting roller unit is coupled rotatable to a rotary shaft which is provided at the support bracket unit.

7. The adaptor of claim 4, wherein a through hole is formed at a portion corresponding to the adjusting roller unit of the housing unit.

8. The adaptor of claim 1, wherein the reflection member is formed of a mirror.

* * * * *